(12) United States Patent
Xu et al.

(10) Patent No.: US 10,611,721 B2
(45) Date of Patent: Apr. 7, 2020

(54) METHOD FOR PREPARING LEVOBUNOLOL HYDROCHLORIDE

(71) Applicants: HANGZHOU NORMAL UNIVERSITY, Hangzhou (CN); HANGZHOU LOOP BIOTECH CO., LTD, Hangzhou (CN)

(72) Inventors: Weiming Xu, Hangzhou (CN); Pengfei Zhang, Hangzhou (CN); Dongxiang Feng, Hangzhou (CN); Lianzhi Tao, Hangzhou (CN)

(73) Assignees: HANGZHOU NORMAL UNIVERSITY, Hangzhou (CN); HANGZHOU LOOP BIOTECH CO., LTD, Hangzhou (CN)

( * ) Notice: Subject to any disclaimer, the term of this patent is extended or adjusted under 35 U.S.C. 154(b) by 0 days.

(21) Appl. No.: 16/163,623

(22) Filed: Oct. 18, 2018

(65) Prior Publication Data

US 2020/0071259 A1 Mar. 5, 2020

(30) Foreign Application Priority Data

Aug. 28, 2018 (CN) .......................... 2018 1 0986539

(51) Int. Cl.
*C07C 213/08* (2006.01)

(52) U.S. Cl.
CPC ........ *C07C 213/08* (2013.01); *C07C 2602/10* (2017.05)

(58) Field of Classification Search
None
See application file for complete search history.

(56) References Cited

U.S. PATENT DOCUMENTS 5,426,227 A 6/1995 Stampa Diez Del Corral

OTHER PUBLICATIONS

Leclerc et al. Eur. J. Med. Chem.—Chim Ther., 1982 (17), 1, p. 69-74.*
Lu, Lu; Zhao, Yan-Ping; Ding, Cong; Wu, Ya-Tian; Zhang, Jin-Song; Jiang, Kun; Peng, Jian-Long; Li, Zong-Tao. "Synthesis of levobunolol hydrochloride." Chinese Journal of Medicinal Chemistry, 2010, 1, 32-35.
Liao, Xincheng; Wu, Xianli; Qu, Lingbo; Wang, Wenzhou. "Improved synthesis of levobunolol hydrochloride." Chinese Journal of Medicinal Chemistry, 2003, 3, 166-167.

* cited by examiner

*Primary Examiner* — Clinton A Brooks
(74) *Attorney, Agent, or Firm* — W&G Law Group LLP

(57) ABSTRACT

The present invention provides a method for preparing levobunolol hydrochloride. In the present invention S-1-tert-butyl-epoxy methylamine is subjected to a substitution reaction with 5-hydroxy-1-tetralone, and acidified to obtain the target product levobunolol hydrochloride. The method provided by the present invention greatly improves the regioselectivity of the reaction, avoids the occurrence of side reactions, and effectively improves the yield and optical purity of levobunolol hydrochloride, with the yield being 87.3%, and the ee value being over 99%.

13 Claims, 2 Drawing Sheets

METHOD FOR PREPARING LEVOBUNOLOL HYDROCHLORIDE

CROSS REFERENCE TO RELATED APPLICATIONS

This application claims priority to Chinese application number 201810986539.7, filed Aug. 28, 2018, with a title of METHOD FOR PREPARING LEVOBUNOLOL HYDROCHLORIDE. The above-mentioned patent application is incorporated herein by reference in its entirety.

TECHNICAL FIELD

The present invention relates to the technical field of pharmaceutical synthesis, and in particular to a method for preparing levobunolol hydrochloride.

BACKGROUND

Levobunolol hydrochloride is a class of non-selective β-receptor blocker with good therapeutic effects on open-angle glaucoma. It has been listed by the US FDA as the drug of first choice for the treatment of glaucoma. As levobunolol hydrochloride is a chiral drug, its existing synthetic routes include chiral resolution (Chinese Journal of Medicinal Chemistry, 2010, 20, 1, 32) or direct asymmetric synthesis (U.S. Pat. No. 5,426,227A; Chinese Journal of Medicinal Chemistry, 2003, 13, 3, 166). However, preparing levobunolol hydrochloride by the chiral resolution method generally has the problem of low synthesis efficiency after the chiral resolution. The direct asymmetric synthesis of levobunolol hydrochloride usually uses chiral epichlorohydrin as a raw material, where since there are two reaction sites when the epichlorohydrin molecule reacts with a nucleophilic reagent (positions 1 and 3, for the racemic epichlorohydrin, the products obtained by reacting at the positions 1 and 3 are identical; but for the chiral epichlorohydrin, the stereo configurations of the products obtained by reacting at positions 1 and 3 are reversed), there is a problem that the optical purity is difficult to control due to poor regioselectivity.

SUMMARY

An objective of the present invention is to provide a method for preparing levobunolol hydrochloride. The method provided by the present invention has a high yield of levobunolol hydrochloride and high optical purity.

To achieve the above objective, the present invention provides the following technical solution:

A method for preparing levobunolol hydrochloride, including the following steps:

mixing 5-hydroxy-1-tetralone with S-1-tert-butyl-epoxymethylamine, an alkaline agent and a solvent, to obtain S-5-(3'-tert-butylamino-2'-hydroxy)-propoxy-3,4-dihydro-1(2H)tetralone through a substitution reaction; and acidifying S-5-(3'-tert-butylamino-2'-hydroxy)-propoxy-3,4-dihydro-1(2H)tetralone to give levobunolol hydrochloride.

Preferably, the method for preparing 5-hydroxy-1-tetralone includes the following steps:

mixing 1,5-dihydroxynaphthalene, a metal catalyst, a reducing agent and an alcohol-water solvent to obtain 5-hydroxy-1-tetralone through a reduction reaction.

Preferably, the metal catalyst includes palladium on carbon or raney nickel; and the mass of the metal catalyst is 0.5% to 10% by mass of 1,5-dihydroxynaphthalene.

Preferably, the reducing agent includes one or more of ammonium formate, sodium formate, potassium formate, formic acid and hydrazine hydrate; and the molar ratio of the reducing agent to 1,5-dihydroxynaphthalene is (1-3):1.

Preferably, the alcohol compound in the alcohol-water solvent includes one or more of methanol, ethanol, n-propanol, isopropanol, n-butanol, isobutanol and sec-butanol; the mass ratio of the alcohol compound to water in the alcohol-water solvent is (0.05-20):1; and the mass ratio of the alcohol-water solvent to 1,5-dihydroxynaphthalene is (5-15):1.

Preferably, the reduction reaction is carried out under normal atmospheric conditions; the temperature of the reduction reaction is 60-120° C.; and the time is 3-9 h.

Preferably, the alkaline agent includes sodium hydroxide, sodium ethoxide, sodium methoxide or potassium hydroxide; and the solvent includes methanol, ethanol, an aqueous methanol solution or an aqueous ethanol solution.

Preferably, the mole ratio of 5-hydroxy-1-tetralone, S-1-tert-butyl-epoxymethylamine to the alkaline agent is 1:(0.8-1.1):(1-3); and the mass ratio of 5-hydroxy-1-tetralone to the solvent is 1:(5-15).

Preferably, the temperature of the substitution reaction is 20-90° C., and the time is 3-12 h.

Preferably, after the acidification, the method further includes:

filtering the system obtained after the acidification under suction, recrystallizing the resultant filter cake with ethanol and drying to give levobunolol hydrochloride.

The present invention provides a method for preparing levobunolol hydrochloride. In the present invention S-1-tert-butyl-epoxy methylamine is subjected to a substitution reaction with 5-hydroxy-1-tetralone, and acidified to obtain the target product levobunolol hydrochloride. The method provided by the present invention greatly improves the regioselectivity of the reaction, avoids the occurrence of side reactions, and effectively improves the yield and optical purity of levobunolol hydrochloride, with the yield being 87.3%, and the ee value being over 99%.

Furthermore, in the present invention an intermediate 5-hydroxy-1-tetralone is prepared by using 1,5-dihydroxynaphthalene as a reaction raw material under normal atmospheric conditions through simple operations, which avoids the problem that it is required to use a pressure vessel when a hydrogenation reduction reaction is conducted under high pressure conditions in the prior art, and achieves a high yield of 5-hydroxy-1-tetralone up to 83.3%.

DETAILED DESCRIPTION

Figure 1:
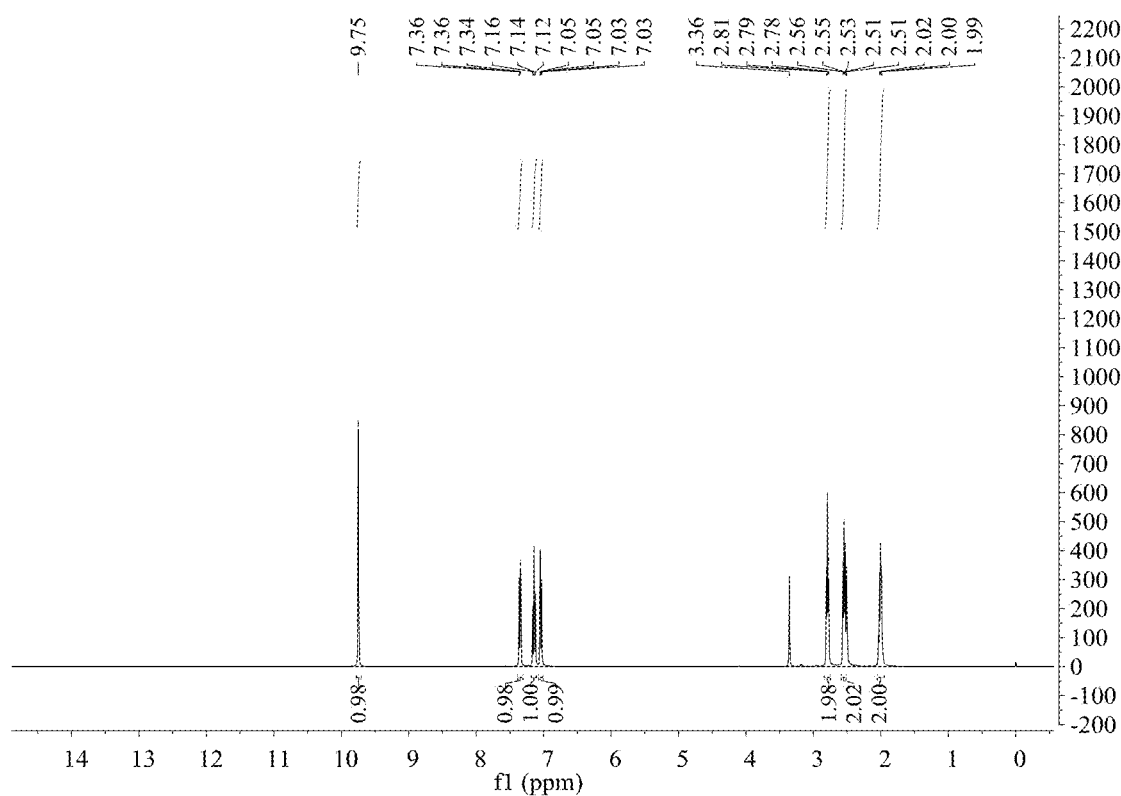
FIG. 1 is $^1$H-nuclear magnetic resonance ($^1$H-NMR) spectrum of 5-hydroxy-1-tetralone prepared in Embodiment 1.

The present invention provides a method for preparing levobunolol hydrochloride, which includes the following steps:

mixing 5-hydroxy-1-tetralone with S-1-tert-butyl-epoxymethylamine, an alkaline agent and a solvent, to obtain S-5-(3'-tert-butylamino-2'-hydroxy)-propoxy-3,4-dihydro-1 (2H)tetralone through a substitution reaction; and acidifying S-5-(3'-tert-butylamino-2'-hydroxy)-propoxy-3,4-dihydro-1(2H)tetralone to give levobunolol hydrochloride.

In the present invention, the method for preparing 5-hydroxy-1-tetralone preferably includes the following steps:

mixing 1,5-dihydroxynaphthalene, a metal catalyst, a reducing agent and an alcohol-water solvent to obtain 5-hydroxy-1-tetralone through a reduction reaction.

In the present invention, the metal catalyst preferably includes palladium on carbon or raney nickel; and the mass of the metal catalyst is preferably 0.5% to 10%, and more preferably 2% to 5% by mass of 1,5-dihydroxynaphthalene. In the present invention, the reducing agent preferably includes one or more of ammonium formate, sodium formate, potassium formate, formic acid and hydrazine hydrate; and the molar ratio of the reducing agent to 1,5-dihydroxynaphthalene is preferably (1-3):1, and more preferably 2:1. In the present invention, the alcohol compound in the alcohol-water solvent preferably includes one or more of methanol, ethanol, n-propanol, isopropanol, n-butanol, isobutanol and sec-butanol; the mass ratio of the alcohol compound to water in the alcohol-water solvent is preferably (0.05-20):1, more preferably (0.5-10):1, and most preferably (2-5):1; and the mass ratio of the alcohol-water solvent to 1,5-dihydroxynaphthalene is preferably (5-15):1, and more preferably (8-12):1.

In the present invention, the reduction reaction is preferably carried out under normal atmospheric conditions; the temperature of the reduction reaction is preferably 60-120° C., and more preferably 80-90° C.; and the time of the reduction reaction is preferably 3-9 h, and more preferably 4-5 h.

In the present invention, after the reduction reaction is completed, the system obtained after the reduction reaction is preferably mixed with sodium hydroxide, and filtered under suction to obtain a filtrate the pH value of which is adjusted to 2-3 with hydrochloric acid. The filtrate is filtered under suction after a solid is precipitated, and the resultant filter cake is recrystallized and dried to obtain 5-hydroxy-1-tetralone. In the embodiments of the present invention, particularly the pH value of the filtrate is adjusted to 2-3 by using an industrial hydrochloric acid having a mass concentration of 31%. In the present invention, utilization of sodium hydroxide is for the purpose of increasing reaction selectivity and keeping the system alkaline, such that the raw material and the product can be dissolved; and utilization of hydrochloric acid is for the purpose of converting 5-hydroxy-1-tetralone sodium salt into 5-hydroxy-1-tetralone, which has reduced solubility and thus is precipitated from the system. In the present invention, the recrystallization agent employed for the recrystallization is preferably a mixture of methanol and water; and the volume ratio of methanol to water is preferably (2-4):1. In the present invention, the drying is preferably vacuum drying; and the present invention has no special requirement on specific operating conditions of the vacuum drying, and vacuum drying operating conditions well known to those skilled in the art may be employed.

In the present invention, after 5-hydroxy-1-tetralone is obtained, 5-hydroxy-1-tetralone is mixed with S-1-tert-butyl-epoxymethylamine, an alkaline agent and a solvent, to obtain S-5-(3'-tert-butylamino-2'-hydroxy)-propoxy-3, 4-dihydro-1(2H)tetralone through a substitution reaction. In the present invention, the mole ratio of 5-hydroxy-1-tetralone, S-1-tert-butyl-epoxymethylamine to the alkaline agent is preferably 1:(0.8-1.1):(1-3), and more preferably 1:1.2; and the mass ratio of 5-hydroxy-1-tetralone to the solvent is preferably 1:(5-15), and more preferably 1:(8-12). The present invention has no special requirement on the source of S-1-tert-butyl-epoxymethylamine, and a method well known to those skilled in the art can be used for preparation; and in the embodiments of the present invention, specifically the preparation is conducted according to the technical solution disclosed in the granted patent: ZL200910070239.5 owned by Asymchem Inc in Tianjin. In the present invention, the alkaline agent preferably includes sodium hydroxide, sodium ethoxide, sodium methoxide or potassium hydroxide. In the present invention, the solvent preferably includes methanol, ethanol, an aqueous methanol solution or an aqueous ethanol solution; and when the solvent is the aqueous methanol solution or the aqueous ethanol solution, the mass ratio of methanol or ethanol to water in the solvent is preferably >90:1, and more preferably (92-98):1.

In the present invention, the temperature of the substitution reaction is preferably 20-90° C., and more preferably 30-50° C.; and the time is preferably 3-12 h, and more preferably 5-6 h.

In the present invention, after completion of the substitution reaction, preferably the solvent is removed from the obtained system, the resultant residue is extracted with a mixture of ethyl acetate and water, the aqueous layer and the organic layer are separated, and the solvent is removed from the resultant organic layer to obtain S-5-(3'-tert-butylamino-2'-hydroxy)-propoxy-3, 4-dihydro-1(2H)tetralone. The present invention has no special requirement on the specific method employed for removing the solvent, and a method for removing the solvent well known to those skilled in the art may be employed; specifically, such as rotary evaporation. In the present invention, the volume ratio of ethyl acetate to water used for the extraction is preferably 1:(0.5-1.5), and more preferably 1:1. In the embodiments of the present invention, particularly the system obtained after the substitution reaction is subjected to rotary evaporation, the resultant residue is extracted with a mixture of ethyl acetate and water (with a volume ratio of ethyl acetate to water of 1:(0.5-1.5)), the aqueous layer and the organic layer are separated, and the organic layer is subjected to rotary evaporation to obtain S-5-(3'-tert-butylamino-2'-hydroxy)-propoxy-3,4-dihydro-1 (2H)tetralone.

In the present invention, after S-5-(3'-tert-butylamino-2'-hydroxy)-propoxy-3,4-dihydro-1 (2H)tetralone is obtained, S-5-(3'-tert-butylamino-2'-hydroxy)-propoxy-3,4-dihydro-1 (2H)tetralone is acidified to give levobunolol hydrochloride. In the present invention, the acidifying agent employed for the acidification is preferably a solution of hydrogen chloride in ethanol; and in the present invention, preferably S-5-(3'-tert-butylamino-2'-hydroxy)-propoxy-3,4-dihydro-1 (2H)tetralone is mixed with the solution of hydrogen chloride in ethanol, and acidified to give levobunolol hydrochloride.

In the present invention, the molar concentration of hydrogen chloride in the solution of hydrogen chloride in ethanol is preferably 1-3 mol/L, and more preferably 2 mol/L; and the solution of hydrogen chloride in ethanol is prepared by introducing dry hydrogen chloride gas into anhydrous ethanol.

In the present invention, the acidification temperature is preferably 20-50° C., and more preferably 30-40° C.; and the time is preferably 1.5-2.5 h, and more preferably 2 h.

In the present invention, after completion of the acidification, preferably the system obtained after the acidification is filtered under suction, and the resultant filter cake is recrystallized with ethanol and dried to give levobunolol hydrochloride. In the present invention, the drying is preferably vacuum drying; and the present invention has no special requirement on specific operating conditions of the vacuum drying, and vacuum drying operating conditions well known to those skilled in the art may be employed.

In the present invention, the reaction route for preparing levobunolol hydrochloride is as follows.

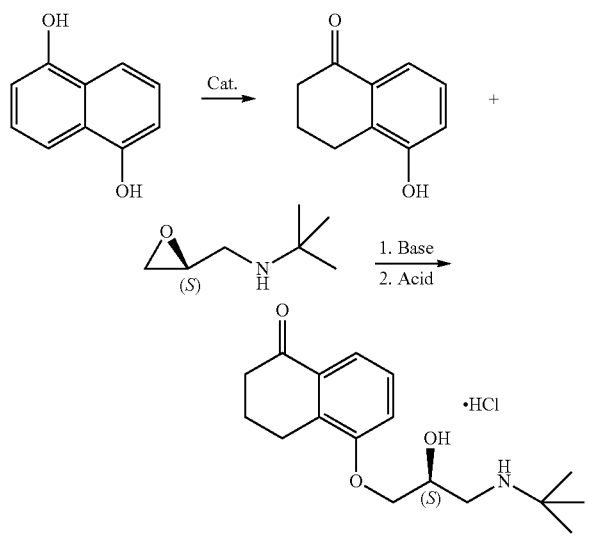

The following clearly and completely describes the technical solutions in the present invention with reference to the embodiments of the present invention. Apparently, the described embodiments are merely a part rather than all of the embodiments of the present invention. All other embodiments obtained by a person of ordinary skill in the art based on the embodiments of the present invention without creative efforts shall fall within the protection scope of the present invention.

Embodiment 1

32 g 1,5-dihydroxynaphthalene, 400 g water, 80 g isopropanol, 0.16 g palladium on carbon and 40.8 g sodium formate were mixed, and heated to 60° C. under normal atmospheric conditions for reduction reaction for 9 h. The resultant system was added with 12 g sodium hydroxide, stirred, and filtered under suction while it was hot. The pH value of the resultant filtrate was adjusted to 2 by using an industrial hydrochloric acid having a mass concentration of 31%. The filtrate was filtered under suction after a solid was precipitated, and the resultant filter cake was recrystallized with a mixture of methanol and water (with the volume ratio of methanol to water of 2:1), and vacuum dried to obtain 23.7 g 5-hydroxy-1-tetralone, with liquid-phase purity greater than 99%, and the yield of 73.1%.

8.1 g 5-hydroxy-1-tetralone, 39.5 g methanol, 2 g sodium hydroxide and 6.44 g S-1-tert-butyl-epoxymethylamine were mixed to conduct an substitution reaction at 20° C. for 12 h. The resultant system was evaporated to dryness, and the resultant residue was extracted with a 80 mL mixture of ethyl acetate and water (with a volume ratio of ethyl acetate to water of 1:1). The aqueous layer and the organic layer were separated and the organic layer was evaporated to dryness. The residue was added with a solution of hydrogen chloride in ethanol (60 mL, where the molar concentration of hydrogen chloride was 1 mol/L), stirred at a condition of 20° C. for 1 h, and filtered under suction. The resultant filter cake was recrystallized with ethanol and vacuum dried to give 11.5 g levobunolol hydrochloride, with liquid-phase purity greater than 99%, an ee value greater than 99%, and the yield of 73.1%.

Figure 2:
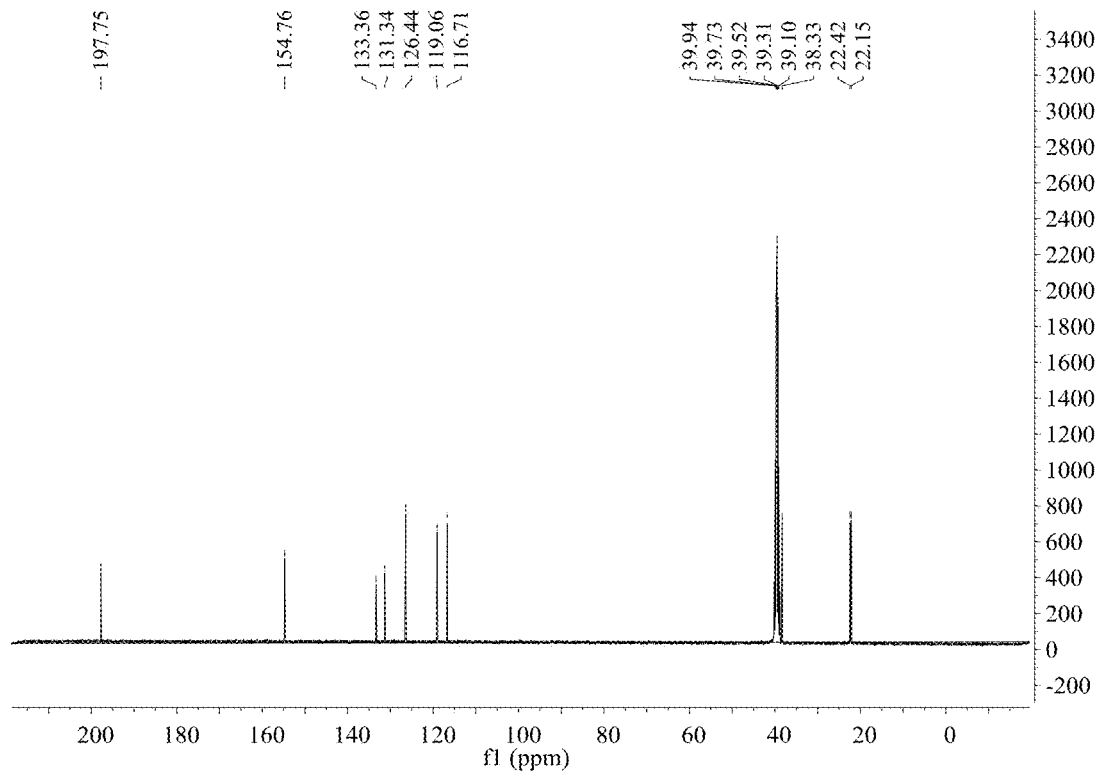
FIG. 2 is $^{13}$C-nuclear magnetic resonance ($^{13}$C-NMR) spectrum of 5-hydroxy-1-tetralone prepared in Embodiment 1.

FIGS. 1 and 2 were nuclear magnetic resonance spectra of 5-hydroxy-1-tetralone prepared in this embodiment. It can be seen from FIGS. 1 and 2 that the product prepared in this embodiment is indeed 5-hydroxy-1-tetralone.

Figure 3:
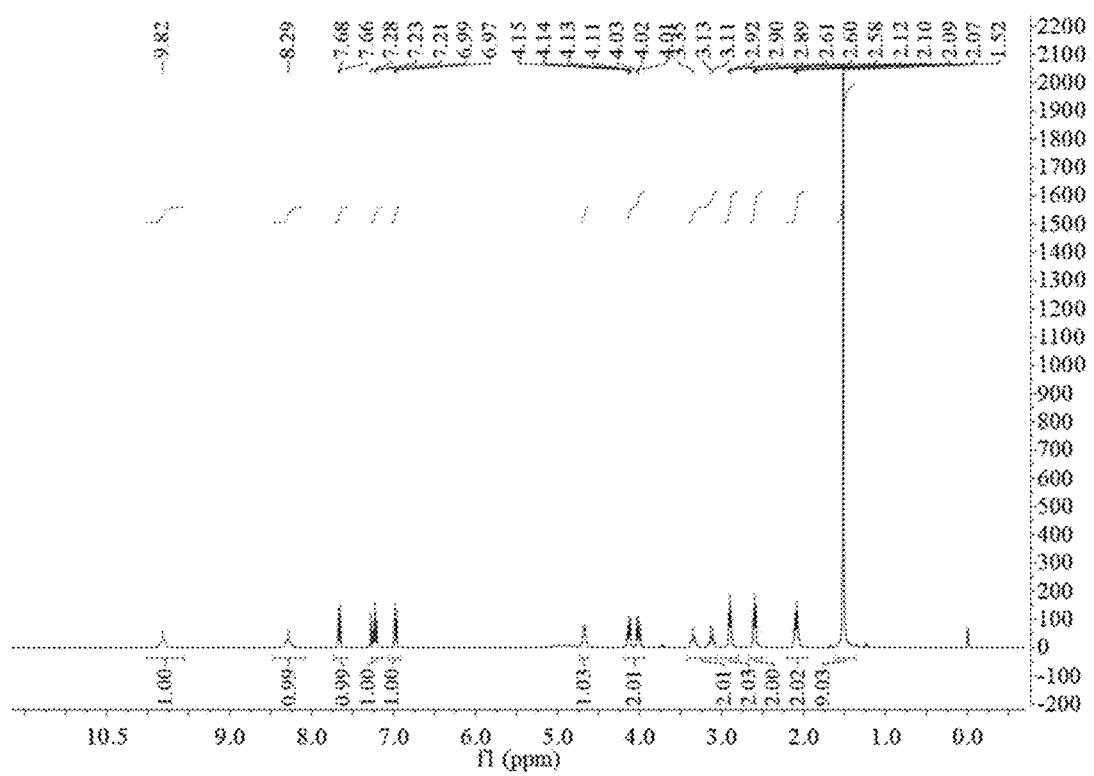
FIG. 3 is $^1$H-nuclear magnetic resonance ($^1$H-NMR) spectrum of levobunolol hydrochloride prepared in Embodiment 1.
Figure 4:
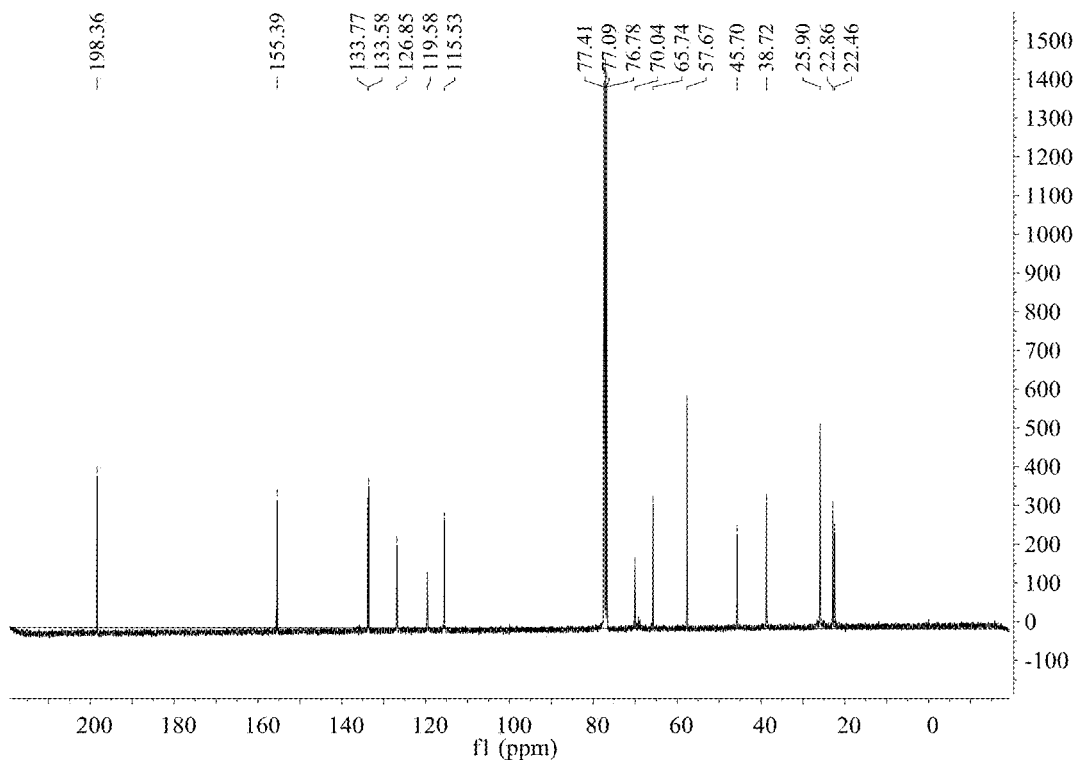
FIG. 4 is $^{13}$C-nuclear magnetic resonance ($^{13}$C-NMR) spectrum of levobunolol hydrochloride prepared in Embodiment 1.

FIGS. 3 and 4 are nuclear magnetic resonance spectra of levobunolol hydrochloride prepared in this embodiment. As can be seen from FIGS. 3 and 4, the product prepared in this embodiment is indeed levobunolol hydrochloride.

Embodiment 2

32 g 1,5-dihydroxynaphthalene, 8 g water, 152 g n-butanol, 3.2 g palladium on carbon and 12.6 g ammonium formate were mixed, and heated to 120° C. under normal atmospheric conditions for reduction reaction for 3 h. The resultant system was added with 12 g sodium hydroxide, stirred, and filtered under suction while it was hot. The pH value of the resultant filtrate was adjusted to 3 by using an industrial hydrochloric acid having a mass concentration of 31%. The filtrate was filtered under suction after a solid was precipitated, and the resultant filter cake was recrystallized with methanol and water (with the volume ratio of methanol to water of 4:1), and vacuum dried to obtain 27.0 g 5-hydroxy-1-tetralone, with liquid-phase purity greater than 99%, and the yield of 83.3%.

8.1 g 5-hydroxy-1-tetralone, 118.5 g methanol, 6 g sodium hydroxide and 8.85 g S-1-tert-butyl-epoxymethylamine were mixed to conduct an substitution reaction at 70° C. for 6 h. The resultant system was evaporated to dryness, and the resultant residue was extracted with a 90 mL mixture of ethyl acetate and water (with a volume ratio of ethyl acetate to water of 2:1). The aqueous layer and the organic layer were separated and the organic layer was evaporated to dryness. The residue was added with a solution of hydrogen chloride in ethanol (30 mL, where the molar concentration of hydrogen chloride was 3 mol/L), stirred at a condition of 50° C. for 1 h, and filtered under suction. The resultant filter cake was recrystallized with ethanol and vacuum dried to give 13.8 g levobunolol hydrochloride, with liquid-phase purity greater than 98%, an ee value greater than 99%, and the yield of 85.4%.

Embodiment 3

32 g 1,5-dihydroxynaphthalene, 10 g water, 200 g ethanol, 1.6 g palladium on carbon, 13.6 g sodium formate and 9.2 g formic acid were mixed, and heated to 90° C. under normal atmospheric conditions for reduction reaction for 6 h. The resultant system was added with 12 g sodium hydroxide, stirred, and filtered under suction while it was hot. The pH value of the resultant filtrate was adjusted to 2.5 by using an industrial hydrochloric acid having a mass concentration of 31%. The filtrate was filtered under suction after a solid was precipitated, and the resultant filter cake was recrystallized with methanol and water (with the volume ratio of methanol to water of 3:1), and vacuum dried to obtain 24.9 g 5-hydroxy-1-tetralone, with liquid-phase purity greater than 99%, and the yield of 76.9%.

8.1 g 5-hydroxy-1-tetralone, 100 g ethanol, 10 g water, 6 g potassium hydroxide and 8.05 g S-1-tert-butyl-epoxymethylamine were mixed to conduct an substitution reaction at 90° C. for 3 h. The resultant system was evaporated to dryness, and the resultant residue was extracted with a 100 mL mixture of ethyl acetate and water (with a volume ratio of ethyl acetate to water of 2:3). The aqueous layer and the organic layer were separated and the organic layer was evaporated to dryness. The residue was added with a solution of hydrogen chloride in ethanol (40 mL, where the molar concentration of hydrogen chloride was 2 mol/L), stirred at a condition of 30° C. for 1 h, and filtered under suction. The resultant filter cake was recrystallized with ethanol and vacuum dried to give 13.3 g levobunolol hydrochloride, with liquid-phase purity greater than 99%, an ee value greater than 99%, and the yield of 82.4%.

Embodiment 4

32 g 1,5-dihydroxynaphthalene, 300 g water, 15 g methanol, 1.2 g palladium on carbon and 42 g potassium formate were mixed, and heated to 70° C. under normal atmospheric conditions for reduction reaction for 6 h. The resultant system was added with 12 g sodium hydroxide, stirred, and filtered under suction while it was hot. The pH value of the resultant filtrate was adjusted to 2 by using an industrial hydrochloric acid having a mass concentration of 31%. The filtrate was filtered under suction after a solid was precipitated, and the resultant filter cake was recrystallized with methanol and water (with the volume ratio of methanol to water of 4:1), and vacuum dried to obtain 24.9 g 5-hydroxy-1-tetralone, with liquid-phase purity greater than 99%, and the yield of 82.4%.

8.1 g 5-hydroxy-1-tetralone, 100 g methanol, 10 g water, 6 g sodium ethoxide and 8.05 g S-1-tert-butyl-epoxymethylamine were mixed to conduct an substitution reaction at 50° C. for 5 h. The resultant system was evaporated to dryness, and the resultant residue was extracted with a 80 mL mixture of ethyl acetate and water (with a volume ratio of ethyl acetate to water of 1:1). The aqueous layer and the organic layer were separated and the organic layer was evaporated to dryness. The residue was added with a solution of hydrogen chloride in ethanol (35 mL, where the molar concentration of hydrogen chloride was 2 mol/L), stirred at a condition of 35° C. for 1 h, and filtered under suction. The resultant filter cake was recrystallized with ethanol and vacuum dried to give 14.1 g levobunolol hydrochloride, with liquid-phase purity greater than 99%, an ee value greater than 99%, and the yield of 87.3%.

Embodiment 5

32 g 1,5-dihydroxynaphthalene, 200 g water, 150 g n-propanol, 1.2 g raney nickel and 25 g hydrazine hydrate were mixed, and heated to 85° C. under normal atmospheric conditions for reduction reaction for 6 h. The resultant system was added with 12 g sodium hydroxide, stirred, and filtered under suction while it was hot. The pH value of the resultant filtrate was adjusted to 2 by using an industrial hydrochloric acid having a mass concentration of 31%. The filtrate was filtered under suction after a solid was precipitated, and the resultant filter cake was recrystallized with methanol and water (with the volume ratio of methanol to water of 3:1), and vacuum dried to obtain 23.7 g 5-hydroxy-1-tetralone, with liquid-phase purity greater than 99%, and the yield of 73.1%.

8.1 g 5-hydroxy-1-tetralone, 80 g ethanol, 2 g water, 6.8 g sodium ethoxide and 8.05 g S-1-tert-butyl-epoxymethylamine were mixed to conduct an substitution reaction at 30° C. for 6 h. The resultant system was evaporated to dryness, and the resultant residue was extracted with a 80 mL mixture of ethyl acetate and water (with a volume ratio of ethyl acetate to water of 1:1). The aqueous layer and the organic layer were separated and the organic layer was evaporated to dryness. The residue was added with a solution of hydrogen chloride in ethanol (30 mL, where the molar concentration of hydrogen chloride was 2 mol/L), stirred at a condition of 25° C. for 1 h, and filtered under suction. The resultant filter cake was recrystallized with ethanol and vacuum dried to give 13.3 g levobunolol hydrochloride, with liquid-phase purity greater than 99%, an ee value greater than 99%, and the yield of 82.4%.

Embodiment 6

32 g 1,5-dihydroxynaphthalene, 200 g water, 150 g isobutanol, 1.2 g palladium on carbon, 13.6 g sodium formate, 10 g hydrazine hydrate, and 12.6 g ammonium formate were mixed, and heated to 90° C. under normal atmospheric conditions for reduction reaction for 6 h. The resultant system was added with 12 g sodium hydroxide, stirred, and filtered under suction while it was hot. The pH value of the resultant filtrate was adjusted to 2 by using an industrial hydrochloric acid having a mass concentration of 31%. The filtrate was filtered under suction after a solid was precipitated, and the resultant filter cake was recrystallized with methanol and water (with the volume ratio of methanol to water of 3:1), and vacuum dried to obtain 26.6 g 5-hydroxy-1-tetralone, with liquid-phase purity greater than 99%, and the yield of 82.1%.

8.1 g 5-hydroxy-1-tetralone, 50 g methanol, 2 g water, 5.4 g sodium methoxide and 8.05 g S-1-tert-butyl-epoxymethylamine were mixed to conduct a substitution reaction at 40° C. for 6 h. The resultant system was evaporated to dryness, and the resultant residue was extracted with a 80 mL mixture of ethyl acetate and water (with a volume ratio of ethyl acetate to water of 1:1). The aqueous layer and the organic layer were separated and the organic layer was evaporated to dryness. The residue was added with a solution of hydrogen chloride in ethanol (40 mL, where the molar concentration of hydrogen chloride was 1.5 mol/L), stirred at a condition of 30° C. for 1 h, and filtered under suction. The resultant filter cake was recrystallized with ethanol and vacuum dried to give 13.6 g levobunolol hydrochloride, with liquid-phase purity greater than 99%, an ee value greater than 99%, and the yield of 84.2%.

Embodiment 7

32 g 1,5-dihydroxynaphthalene, 200 g water, 150 g sec-butanol, 1.2 g palladium on carbon, 13.6 g sodium formate and 25.2 g ammonium formate were mixed, and heated to 80° C. under normal atmospheric conditions for reduction reaction for 6 h. The resultant system was added with 12 g sodium hydroxide, stirred, and filtered under suction while it was hot. The pH value of the resultant filtrate was adjusted to 2 by using an industrial hydrochloric acid having a mass concentration of 31%. The filtrate was filtered under suction after a solid was precipitated, and the resultant filter cake was recrystallized with methanol and water (with the volume ratio of methanol to water of 4:1), and vacuum dried to obtain 25.9 g 5-hydroxy-1-tetralone, with liquid-phase purity greater than 99%, and the yield of 79.9%.

8.1 g 5-hydroxy-1-tetralone, 100 g methanol, 8 g water, 3.5 g sodium ethoxide and 8.05 g S-1-tert-butyl-epoxymethylamine were mixed to conduct an substitution reaction at 40° C. for 6 h. The resultant system was evaporated to dryness, and the resultant residue was extracted with a 80 mL mixture of ethyl acetate and water (with a volume ratio of ethyl acetate to water of 1:1). The aqueous layer and the organic layer were separated and the organic layer was evaporated to dryness. The residue was added with a solution of hydrogen chloride in ethanol (35 mL, where the molar concentration of hydrogen chloride was 2 mol/L), stirred at a condition of 40° C. for 1 h, and filtered under suction. The resultant filter cake was recrystallized with ethanol and vacuum dried to give 13.8 g levobunolol hydrochloride, with liquid-phase purity greater than 99%, an ee value greater than 99%, and the yield of 85.4%.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A method for preparing levobunolol hydrochloride, comprising the following steps:
    mixing 5-hydroxy-1-tetralone with S-1-tert-butyl-epoxymethylamine, an alkaline agent and a solvent, to obtain S-5-(3'-tert-butylamino-2'-hydroxy)-propoxy-3,4-dihydro-1(2H)tetralone through a substitution reaction; and
    acidifying S-5-(3'-tert-butylamino-2'-hydroxy)-propoxy-3,4-dihydro-1 (2H)tetralone to give levobunolol hydrochloride;
    wherein the method for preparing 5-hydroxy-1-tetralone comprises the following steps:
    mixing 1,5-dihydroxynaphthalene a metal catalyst, a reducing agent and an alcohol-water solvent to obtain 5-hydroxy-1-tetralone through a reduction reaction;
    wherein the reducing agent comprises one or more of ammonium formate, sodium formate, potassium formate, formic acid and hydrazine hydrate; and the molar ratio of the reducing agent to 1,5-dihydroxynaphthalene is (1-3):1.

2. The preparation method of claim 1, wherein the metal catalyst comprises palladium on carbon or raney nickel; and the mass of the metal catalyst is 0.5% to 10% by mass of 1,5-dihydroxynaphthalene.

3. The preparation method of claim 2, wherein the reduction reaction is carried out at approximately 101 KPa; the temperature of the reduction reaction is 60-120° C.; and the time is 3-9 h.

4. The preparation method of claim 1, wherein the alcohol compound in the alcohol-water solvent comprises one or more of methanol, ethanol, n-propanol, isopropanol, n-butanol, isobutanol and sec-butanol; the mass ratio of the alcohol compound to water in the alcohol-water solvent is (0.05-20):1; and the mass ratio of the alcohol-water solvent to 1,5-dihydroxynaphthalene is (5-15):1.

5. The preparation method of claim 4, wherein the reduction reaction is carried out at approximately 101 KPa; the temperature of the reduction reaction is 60-120° C.; and the time is 3-9 h.

6. The preparation method of claim 1, wherein the reduction reaction is carried out at approximately 101 KPa; the temperature of the reduction reaction is 60-120° C.; and the time is 3-9 h.

7. The preparation method of claim 1, wherein the alkaline agent comprises sodium hydroxide, sodium ethoxide, sodium methoxide or potassium hydroxide; and the solvent comprises methanol, ethanol, an aqueous methanol solution or an aqueous ethanol solution.

8. The preparation method of claim 7, wherein the temperature of the substitution reaction is 20-90° C., and the time is 3-12 h.

9. The preparation method of claim 1, wherein the mole ratio of 5-hydroxy-1-tetralone, S-1-tert-butyl-epoxymethylamine to the alkaline agent is 1:(0.8-1.1):(1-3); and the mass ratio of 5-hydroxy-1-tetralone to the solvent is 1:(5-15).

10. The preparation method of claim 9, wherein the temperature of the substitution reaction is 20-90° C., and the time is 3-12 h.

11. The preparation method of claim 1, wherein the temperature of the substitution reaction is 20-90° C., and the time is 3-12 h.

12. The preparation method of claim 1, further comprising after the acidification:
    filtering the system obtained after the acidification under suction, recrystallizing the resultant filter cake with ethanol and drying to give levobunolol hydrochloride.

13. The preparation method of claim 1, wherein the reduction reaction is carried out at approximately 101 KPa; the temperature of the reduction reaction is 60-120° C.; and the time is 3-9 h.

* * * * *